United States Patent [19]

Shiokawa et al.

[11] Patent Number: 4,806,553

[45] Date of Patent: Feb. 21, 1989

[54] PYRIDYL ALKYLENEDIAMINE COMPOUNDS INSECTICIDAL

[75] Inventors: Kozo Shiokawa, Kawasaki; Shinichi Tsuboi, Hino; Shinzo Kagabu, Gifu; Shoko Sasaki, Hino; Koichi Moriya, Tokyo; Yumi Hattori, Hachioji, all of Japan

[73] Assignee: Nihon Tokushu Noyaku Seizo K.K., Tokyo, Japan

[21] Appl. No.: 64,267

[22] Filed: Jun. 18, 1987

[30] Foreign Application Priority Data

Jul. 1, 1986 [JP] Japan .................. 61-152763

[51] Int. Cl.⁴ ............. A61K 31/44; C07D 213/26; C07D 212/26; C07D 213/28
[52] U.S. Cl. ................. 514/332; 514/336; 514/345; 514/346; 514/348; 514/351; 546/261; 546/264; 546/266; 546/290; 546/291; 546/293; 546/296; 546/300; 546/301; 546/302; 546/303; 546/329; 546/330; 546/331; 546/332; 546/334
[58] Field of Search .......... 546/266, 290, 300, 329, 546/330, 331, 332, 334, 261, 264, 291, 293, 296, 301, 302, 303; 514/333, 345, 349, 357, 332, 336, 346, 348, 351

[56] References Cited

U.S. PATENT DOCUMENTS 4,060,621 11/1977 Durant et al. .............. 546/300

FOREIGN PATENT DOCUMENTS 1397436 6/1975 United Kingdom .......... 546/300
1421792 1/1976 United Kingdom .......... 546/300

Primary Examiner—Mary C. Lee
Assistant Examiner—Zinna Northington
Attorney, Agent, or Firm—Sprung Horn Kramer & Woods

[57] ABSTRACT

There are provided insecticidally active alkylenediamines of the formula

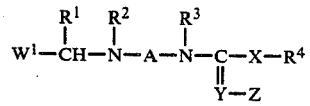

wherein $W^1$ stands for a 5- or 6-membered heterocyclic group which may be substituted, containing at least one hetero atom selected from, O, S and N, $R^1$, $R^2$ and $R^3$ are hydrogen or alkyl and $R^4$, X, Y and Z have the meanings as given in the specification.

The new alkylenediamines can be prepared according to different preparation methods and exhibit a strong insecticidal activity.

5 Claims, No Drawings

PYRIDYL ALKYLENEDIAMINE COMPOUNDS INSECTICIDAL

The present invention relates to novel alkylenediamines, to processes for their preparation and to their use as insecticides.

There have now been found novel alkylenediamines of the formula (I)

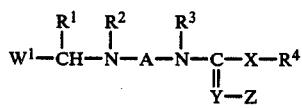

wherein
- $W^1$ is a 5- or 6-membered heterocyclic group which may be substituted, containing at least one hetero atom selected from O, S and N, and
- $R^1$, $R^2$ and $R^3$ are hydrogen or alkyl,
- $R^4$ is hydrogen, alkyl, aryl, aralkyl, alkoxy, dialkylamino, alkoxyalkyl, alkylthioalkyl or $-CH_2-W^2$ in which $W^2$ has the same meanings as $W^1$ stated above
- X is S,

or a single bond, in which $R^5$ is hydrogen or alkyl, in the case where X is

the group

in the formula (I) may have the same meaning as the group

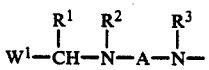

in formula (I),
Y is N or

in which $R^6$ is hydrogen, alkyl, aryl, acyl, alkoxycarbonyl or cyano,
Z is cyano or nitro, and
A is ethylene or trimethylene which may be substituted by alkyl.

The compounds of the formula (I) are obtained by a process in which, (a) in the case where X is S and $R^4$ has meanings other than "alkoxy" and "dialkylamino" in the definitions, and for which case in the following formula (III) $R^4$ is replaced by the symbol $R^7$, provided that the two $R^7$'s are not hydrogen at the same time:

Compounds of the formula (II)

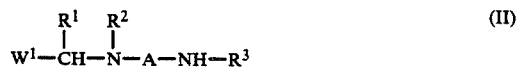

wherein $R^1$, $R^2$, $R^3$, $W^1$ and A are as defined, are reacted with compounds of the formula (III)

wherein Y, Z and $R^7$ are as defined, in the presence of inert solvents, or (b) in the case where X is

Compounds of the formula (IV)

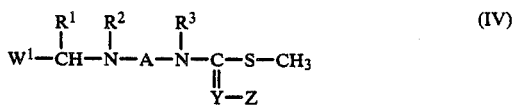

wherein $R^1$, $R^2$, $R^3$, Y, Z, $W^1$ and A are as defined, are reacted with compounds of the formula (V)

wherein $R^4$ and $R^5$ are as defined, in the presence of inert solvents, or (c) in the case where X is

and Y is N:
aforesaid compounds of the formula (II) are reacted with compounds of the formula (VI)

wherein $R^4$, $R^5$ and Z are as defined, in the presence of inert solvents, or (d) in the case where Y is

X is a single bond and $R^4$ is replaced by the symbol $R^7$ hereinbefore: aforesaid compounds of the formula (II) are reacted with compounds of the formula (VII)

$$Z-\underset{R^6}{\underset{|}{CH}}-\overset{O}{\overset{\|}{C}}-R^7 \qquad (VII)$$

wherein $R^6$, $R^7$ and Z are as defined above, in the presence of inert solvents, or (e) in the case where X is S and $R^4$ has other meanings than "hydrogen", "alkoxy" and "dialkylamino" in the definitions, and for which case in the following formula (IX) $R^4$ is replaced by the symbol $R^8$:

Compounds of the formula (VIII)

$$W^1-\underset{R^1}{\underset{|}{CH}}-\underset{R^2}{\underset{|}{N}}-A-\underset{R^3}{\underset{|}{N}}-\underset{\underset{Z}{\overset{\|}{Y}}}{C}-SH \qquad (VIII)$$

wherein $R^1$, $R^2$, $R^3$, Y, Z and $W^1$ are as defined, are reacted with compounds of the formula (IX)

$$Hal-R^8 \qquad (IX)$$

wherein $R^8$ is as defined, and Hal represents halogen, in the presence of inert solvents and if appropriate in the presence of base.

The novel alkylenediamines exhibit powerful insecticidal properties, in particular, against sucking insects typified by insects of Hemiptera, such as aphids, planthoppers and leafhoppers, which have acquired resistance to organic phosphate and carbamate type-insecticides caused by having been used throughout long term. The novel alkylenediamines of formula (I) are surprisingly effective as insecticides.

Among the novel alkylenediamines according to the invention, of the formula (I), preferred compounds are those in which $W^1$ represents a 5 or 6-membered heterocyclic group containing 1 to 3 hetero atoms selected from O, S and N at least one of which is N, the group $W^1$ being optionally substituted by at least one substituent selected from halogen, $C_{1-4}$-alkyl, $C_{1-4}$-alkoxy, $C_{1-4}$-alkylthio, $C_{1-4}$-haloalkyl and $C_{1-4}$-haloalkoxy and $R^1$, $R^2$ and $R^3$ represent hydrogen or $C_{1-4}$ alkyl, $R^4$ represents hydrogen, $C_{1-4}$ alkyl, $C_{6-10}$ aryl, benzyl, phenethyl, $C_{1-4}$ alkoxy, dialkylamino having 2 to 6 carbon atoms in total, alkoxyalkyl having 2 to 6 carbon atoms in total, alkylthioalkyl having 2 to 4 carbon atoms in total or a group of the formula $-CH_2-W^2$ in which $W^2$ has the same meanings as $W^1$ stated hereinafter, X represents S or $$-\underset{R^5}{\underset{|}{N}}-,$$

in which $R^5$ represents hydrogen or $C_{1-4}$ alkyl, in the case where X represents $$-\underset{R^5}{\underset{|}{N}}-,$$

the group $$-\underset{R^5}{\underset{|}{\overset{R^4}{\overset{|}{N}}}}-$$

in the formula (I) may have the same meaning as the group $$W^1-\underset{R^1}{\underset{|}{CH}}-\underset{R^2}{\underset{|}{N}}-A-\underset{R^3}{\underset{|}{N}}-$$

in the formula (I),

Y represents N or $$=\underset{R^6}{\underset{|}{C}}-$$

in which $R^6$ represents hydrogen, $C_{1-4}$alkyl, $C_{6-10}$aryl, $C_{1-4}$alkylcarbonyl, alkoxycarbonyl having $C_{1-4}$alkoxy or cyano, Z represents cyano or nitro, and A represents ethylene which may optionally be substituted by methyl or trimethylene which may optionally be substituted by methyl.

Very particularly preferred novel alkylenediamines of the formula (I) are those in which $R^1$, $R^2$ and $R^3$ represent hydrogen, methyl or ethyl, $R^4$ represents hydrogen, methyl, ethyl, phenyl, benzyl, methoxy, dimethylamino, 1-ethoxyethyl, 1-ethyl-thioethyl or 2-chloro-5-pyridylmethyl, X represents S or $$-\underset{R^5}{\underset{|}{N}}-$$

in which $R^5$ represents hydrogen or methyl,

Y represents N or $$=\underset{R^6}{\underset{|}{C}}-$$

in which $R^6$ represents hydrogen, methyl, phenyl, acetyl, ethoxycarbonyl or cyano, Z represents cyano or nitro, $W^1$ represents a 5 or 6-membered heterocyclic group containing 1 to 2 hetero atoms selected from O, S and N at least one of which is N, the group $W^1$ being optionally substituted by at least one substituent selected from fluoro, chloro, bromo, methyl, methoxy, methylthio, trifluoromethyl and trifluoromethoxy, and A represents ethylene or trimethylene.

Specific examples of compounds of formula (I) particularly include i.a.:

N-(2-chloro-5-pyridylmethyl)-N-methyl-N'-(1-methylthio-2-nitrovinyl)ethylenediamine, N-(2-chloro-5-pyridylmethyl)-N-ethyl-N'-(1-methylthio-2-nitrovinyl)ethylenediamine, N-(2-chloro-5-pyridylmethyl)-N'-(1-mercapto-2-nitrovinyl)ethylenedamine, N-(2-chloro-5-pyridylmethyl)-N'-(1-mercapto-2-nitrovinyl)trimethylenediamine, N-(2-chloro-5-pyridylmethyl)-N-methyl-N'-(1-ethylthio-2-nitrovinyl)ethylenediamine, and
N-(2-chloro-5-pyridylmethyl)-N-methyl-N'-(1-propylthio-2-nitrovinyl)ethylenediamine.

When in process (a), N-(2-chloro-5-pyridylmethyl)-N-methylethylenediamine and 1-nitro-2,2-bis(methylthio)ethylene, for example, are used as starting materials, the process is shown by the following reaction scheme.

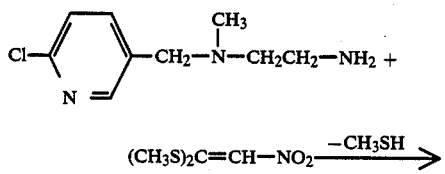

$(CH_3S)_2C=CH-NO_2 \xrightarrow{-CH_3SH}$

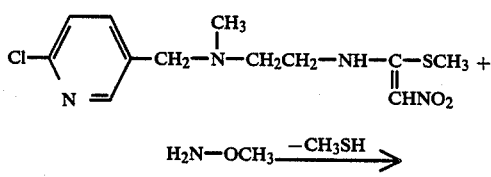

When in process (b) N-(2-chloro-5-pyridylmethyl)-N-methyl-N'-(1-methylthio-2-nitrovinyl)ethylenediamine and O-methylhydroxylamine, for example, are used as starting materials, the process is shown by the following reaction scheme.

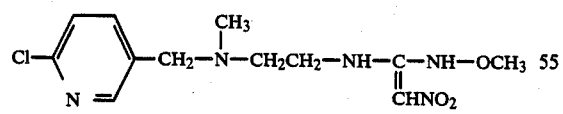

$H_2N-OCH_3 \xrightarrow{-CH_3SH}$

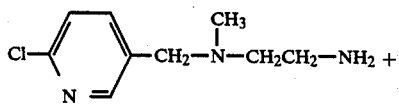

When in process (c) N-(2-chloro-5-pyridylmethyl)-N-methylethylenediamine and N,N-dimethyl-nitroguanidine are used as starting materials, for example, the process is shown by the following reaction scheme.

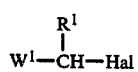

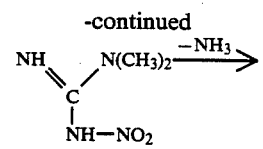

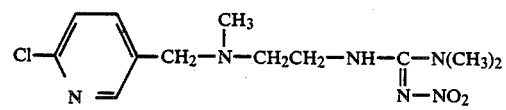

When in process (d), N-(2-chloro-5-pyridylmethyl)-N-methylethylenediamine and nitroacetone, for example, are used as starting materials, the process is shown by the following reaction scheme.

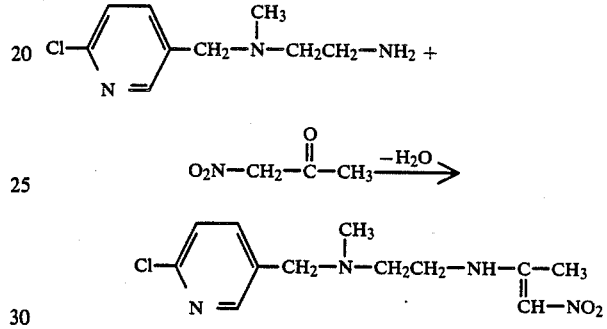

When in process (e) N-(2-chloro-5-pyridylmethyl)-N'-(1-mercapto-2-nitrovinyl)ethylenediamine and 2-chloro-5-chloromethylpyridine, for example, are used as starting materials, the process is shown by the following reaction scheme.

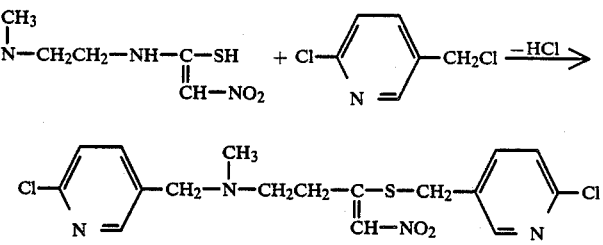

The compound of formula (II) used as a starting material in process (a) mean compounds based on the above definitions of $R^1$, $R^2$, $R^3$, $W^1$ and A above, preferably the above preferred definitions.

The compounds of formula (II) include both novel and known compounds, and can be easily synthesized, for example, by the following general process.

Process (f)

A process for producing the compounds of formula (II), which comprises reacting a compound of the formula $$\begin{array}{c} R^1 \\ | \\ W^1-CH-Hal \end{array} \qquad (X)$$

wherein $R^1$, $W^1$ and Hal are as defined above, with a compound of the formula $$R^2-NH-A-NH-R^3 \qquad (XI)$$

wherein $R^2$, $R^3$ and A are as defined hereinabove.

The compound of formula (X) as a starting material in process (f) were already disclosed in Japanese Patent Applications Nos. 26020/1984 (Laid-Open Patent Publication No. 172976/1985), 72966/1984 (Laid-Open Patent Publication No. 218386/1985), 132943/1984 (Laid-Open Patent Publication No. 12682/1986), 18627/1985, 18628/1985, 23683/1985, 106583/1985, and 106854/1985 filed by the same applicant as in the present application.

The compounds of formula (XI) as a starting material were known in the field of organic chemistry before the filing of the present application. For example, N-methylethylenediamine is known from J. Am. Chem. Soc., Vol. 73, pages 1370–1371, 1951.

The above process (f) can be easily practiced as shown in Examples given hereinafter, and the desired compound of formula (II) as a starting material in process (a) can be obtained.

Specific examples of the compounds of formula (II) are
N-(2-chloro-5-pyridylmethyl)-N-methylethylenediamine,
N-(2-chloro-5-pyridylmethyl)-N-ethylethylenediamine,
N-(2-chloro-5-pyridylmethyl)ethylenediamine, and
N-(2-chloro-5-pyridylmethyl)trimethylenediamine.

Likewise, in process (a), the starting compound of formula (III) means compounds based on the definitions of $R^7$, Y and Z, preferably the aforesaid preferred definitions of Y and Z and the preferred definition of $R^4$ as $R^7$.

The compounds of formula (III) include known compounds already described in Japanese Patent Applications Nos. 219082/1985 and 48629/1986 filed by the same applicant as in the present application. Specific examples include 1-nitro-2,2-bis(methylthio)ethylene, 1-nitro-2,2-bis(ethylthio)ethylene, and dimethylcyanodithioimidecarbonate.

The formula (III), in the case where one of the two $R^7$'s is hydrogen, can assume the following resonance structures:

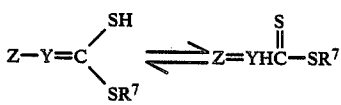

Specifically, a compound having the right formula above, in the case where Z is nitro and Y is —CH=, corresponds to just an ester of nitrodithioacetic acid which is a known compound shown in Chem. Ber., vol. 100, page 591.

The compounds of formula (IV) as a starting material in process (b) mean compounds based on the above definitions of $R^1$, $R^2$, $R^3$, Y, Z, $W^1$ and A, preferably the preferred definitions of $R^1$, $R^2$, $R^3$, Y, Z, $W^1$ and A given above.

Most of the compounds of formula (IV) are included within the compounds of formula (I) in accordance with this invention which are synthesized by process (a) given above.

The compounds of formula (V) which is likewise a starting material means compounds based on the above definitions of $R^4$ and $R^5$, preferably the aforesaid preferred definitions of $R^4$ and $R^5$.

The compounds of formula (V) are well known in the field of organic chemistry.

The compounds of formula (II) used as a starting material in process (c) are synonymous with the compound of formula (II) used in process (a) above.

Likewise, the compounds of formula (VI) as a starting material means compounds based on the above definitions of $R^4$, $R^5$ and Z, preferably the above preferred definitions of $R^4$, $R^6$ and Z.

The compounds of formula (VII) are well known in the field of organic chemistry, and specific examples include nitroguanidine and cyanolguanidine. N-substitution products of these compounds are also known compounds described, for example, in U.S. Pat. No. 2,559,085, J. Am. Chem. Soc., vol. 71, pages 1968–1970, 1949, and British Pat. No. 599,722.

The compounds of formula (II) as a starting material in process (d) are synonymous with the compounds of formula (II) in process (a).

Likewise, the compounds of formula (VII) used as a starting material mean compounds based on the above definitions of $R^6$, $R^7$, and Z, preferably the aforesaid preferred definitions.

The compounds of formula (VII) include known compounds, and are described, for example, in Synthesis, 1979, pages 295–296, and J. Org. Chem., vol. 20, pages 927–936, 1955. Specific examples are 1-nitro-2-propanone, 2-nitroacetophenone and 3-nitro-2-butanone.

The compounds of formula (VIII) as a starting material in process (e) mean compounds based on the above definitions of $R^1$, $R^2$, $R^3$, Y, Z and $W^1$, preferably the aforesaid preferred definitions of these symbols.

The compounds of formula (VIII) are included within the compounds of this invention represented by formula (I) which are synthesized by process (a).

The compounds of formula (IX) used likewise as a starting material mean compounds based on the definitions of $R^8$ and Hal, preferably the preferred definitions of $R^4$ corresponding to $R^8$ and chloro and bromo as Hal.

Specific examples of the compound of formula (XI) are benzyl chloride, and 2-chloro-5-chloromethylpyridine.

In the practice of process (a), all inert organic solvents may be cited as suitable diluents.

Examples of such diluents include water, aliphatic, alicyclic and aromatic hydrocarbons (optionally chlorinated) such as hexane, cyclohexane, petroleum ether, ligroin, benzene, toluene, xylene, melthylene chloride, chloroform, carbon tetrachloride, ethylene chloride and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; and acid amides such as dimethylformamide and dimethylacetamide; sulfones and sulfoxides such as dimethyl sulfoxide and sulfolane; and bases such as pyridine.

Process (a) can be practiced over a substantially broad temperature range, for example at temperatures between about 0° C. and about 100° C., preferably between about 20° C., and about 80° C.

Desirably, the reaction is carried out under atmospheric pressure, but it is also possible to operate under elevated or reduced pressure.

In practicing the process (a), the desired compounds of formula (I) can be obtained by heating 1 mole of the compounds of formula (II) and 1 mole or slightly more than 1 mole of the compound of formula (II), for example, under reflux in an inert solvent until the generation of mercaptan ceases.

In the practice of process (b), the same inert solvents as exemplified with respect to process (a) can be cited as suitable diluents.

Process (b) can be practiced over a broad temperature range, for example at a temperature between about 0° C. and about 150° C., preferably between about 20° C. and about 90° C.

The reaction is preferably carried out under atmospheric pressure, but it may also be carried out under elevated or reduced pressure.

In practicing process (b), the desired compounds of formula (I) can be obtained by heating the compound of formula (IV) and the compounds of formula (V) under reflux in an inert solvent in the same way as in process (a).

In the practice of process (c), the same inert solvents as exemplified with respect to process (a) may be cited as suitable diluents.

Process (c) can be practiced over a wide temperature range, for example at temperatures between about 0° C. and about 150° C., preferably between about 20° C. and about 90° C.

The reaction is preferably carried out under atmospheric pressure, but it can also be carried out under elevated or reduced pressure.

In practicing the process (c), the desired compounds of formula (I) can be obtained by reacting 1 mole of the compounds of formula (II) and 1 mole to slightly more than one mole of the compound of formula (VI), for example, in an inert solvent and as required under acidic conditions.

In the practice of process (d), the same inert solvent as exemplified with respect to process (a) may be cited as suitable diluents.

Process (d) can be practiced over a wide temperature range, for example at temperatures between bout 0° C. and about 150° C., preferably about 20° C. and about 100° C.

The reaction is preferably carried out under atmospheric pressure, but it can also be carried out under elevated or reduced pressure.

In the practice of process (d), the desired compound of formula (I) can be obtained by heating 1 mole of the compounds of formula (II) and 1 mole to slightly more than 1 mole of the compounds of formula (VII), for example, under reflux in an inert solvent while removing by-product water.

In the practice of process (e), the same inert solvents as exemplified above with respect to process (a) may be cited as suitable diluents.

Process (e) can be practiced over a wide temperature range, for example between about 0° C. and about 150° C., preferably between about 20° C. and about 80° C.

The reaction is preferably carried out under atmospheric pressure, but it can also be carried out under elevated or reduced pressure.

In practicing process (e), the desired compounds of formula (I) may be obtained by reacting 1 mole of the compounds of formula (VIII) and 1 mole to slightly more than 1 mole of the compound of formula (IX), for example, in an inert solvent, preferably in the presence of a base.

In the case where the group $-X-R^4$ in the compounds of formula (I) in accordance with this invention is $-SH$, the compounds of this invention can assume a tautomeric resonance structure shown below.

$$W^1-\underset{\underset{R^1}{|}}{C}H-\underset{}{N}-A-\underset{\underset{R^3}{|}}{N}-\underset{\underset{Y-Z}{\|}}{C}-SH \rightleftharpoons W^1-\underset{\underset{R^1}{|}}{C}H-\underset{}{N}-A-\underset{\underset{R^3}{|}}{N}-\underset{\underset{Z}{|}}{\overset{\overset{S}{\|}}{C}}-YH$$

Furthermore, the compounds of this invention can assume a tautomeric resonance structure shown below, in the case where the gorup $-X-R^4$ is $-NHR^5$.

$$W^1-\underset{\underset{R^1}{|}}{C}H-\underset{}{N}-A-\underset{\underset{R^3}{|}}{N}-\underset{\underset{Y-Z}{\|}}{C}-NHR^5 \rightleftharpoons W^1-\underset{\underset{R^1}{|}}{C}H-\underset{}{N}-A-\underset{\underset{R^3}{|}}{N}-\underset{\underset{YH-Z}{|}}{C}=N-R^5$$

In the case where $R^3$ is H, the compounds of this invention can assume the following tautomeric resonance structures.

$$W^1-\underset{\underset{R^1}{|}}{C}H-\underset{}{N}-A-NH-\underset{\underset{Y-Z}{\|}}{C}-X-R^4 \rightleftharpoons W^1-\underset{\underset{R^1}{|}}{C}H-\underset{}{N}-A-N=\underset{\underset{YH-Z}{|}}{C}-X-R^4$$

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus Asellus, Armadillidium vulgare* and *Porcellio scaber;* from the class of the Diplopoda, for example *Blaniulus guttulatus;* from the class of the Chilopoda, for example *Geophilus carophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domesticus,* Grylloptalpa spp., *Locusta migrato ria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*

In the field of veterinary medicine, the novel compounds of this invention are effective against various noxious animal parasites (endo- and ecto-parasites) such as insects and worms.

Examples of such animal parasites are insects such as Gastrophilus spp., Stomoxys spp., Trichodectes spp., Rhodnius spp., and *Ctenocephalides canis.*

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are preferably suitable aromatic hydrocarbons, such as xylene, toluene or alkyl naphthalenes, chlorinated aromatic or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants in the formulations such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general, contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention can be exemplified by the following examples, but the invention shall by no means be deemed to be restricted solely to those examples.

Preparation Examples

EXAMPLE 1

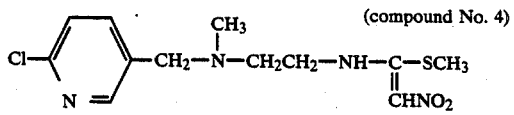

(compound No. 4)

A mixture of N-(2-chloro-5-pyridylmethyl)-N-methylethylenediamine (2.0 g), 1-nitro-2,2-bis(methylthio)ethylene (1.7 g) and ethanol (40 ml) was refluxed for 5 hours with stirring. The reaction mixture was concentrated to about half of its volume, and cooled. The precipitated crystals were collected by filtration, washed with a small amount of ethanol, and dried to give the desired N-(2-chloro-5-pyridylmethyl)-N-methyl-N'-(1-methylthio-2-nitrovinyl)ethylenediamine (1.8 g) having a melting point of 93° to 95° C.

EXAMPLE 2

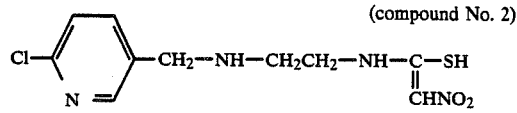

(compound No. 2)

N-(2-chloro-5-pyridylmethyl)ethylenediamine (2.0 g) and methyl 2-nitrodithioacetate (1.7 g) were dissolved in methanol (40 ml), and the solution was heated at 50° C. for 1 hour in a stream of nitrogen. The solution was cooled to room temperature whereupon crystals were precipitated. The crystals were collected by filtration, washed with a small amount of methanol, and then dried to give the desired N-(2-chloro-5-pyridylmethyl)-N'-(1-mercapto-2-nitrovinyl)ethylenediamine (1.2 g) having a melting point of 136° to 137° C. (decomp.).

EXAMPLE 3

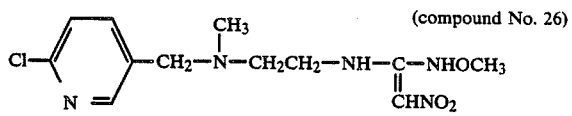

(compound No. 26)

To a solution of 0.95 g of the compound synthesized in Example 1 above in 30 ml of ethanol was added O-methylhydroxylamine (0.16 g), and the mixture was heated under reflux for 1 hour. The ethanol was evaporated under reduced pressure, and the residue was purified by silica gel column chromatography to give the desired N-(2-chloro-5-pyridylmethyl)-N-methyl-N'-(1-methoxyamino-2-nitrovinyl)ethylenediamine (0.6 g) having an $n_D^{20}$ of 1.5466.

EXAMPLE 4

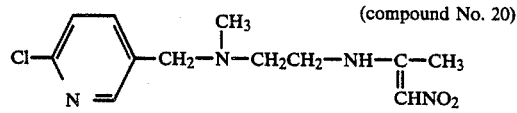

(compound No. 20)

Nitroacetone (1.1 g) and N-(2-chloro-5-pyridylmethyl)-N-methylethylenediamine (2.0 g) were dissolved in toluene (60 ml), and the solution was refluxed for 3 hours in a flask equipped with a water separating device while removing water formed by the reaction. Toluene was concentrated under reduced pressure, and the remaining solid was recrystallized from ethanol to give the desired N-(2-chloro-5-pyridylmethyl)-N-methyl-N'-(1-methyl-2-nitrovinyl)ethylenediamine (2.0 g) having a melting point of 78° to 80° C.

EXAMPLE 5

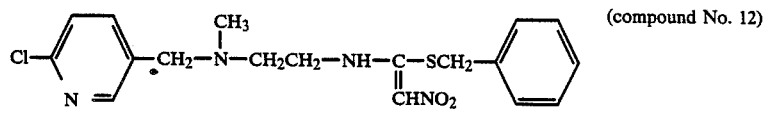

(compound No. 12)

The compound synthesized in Example 2 (1.4 g) was dissolved in dry acetonitrile (30 ml), and potassium carbonate (1.4 g) was added. The mixture was stirred at room temperature for 30 minutes. Then, benzyl bromide (0.9 g) was added, and the mixture was heated at 50° C. for 2 hours with stirring. The reaction mixture was cooled to room temperature, and poured into water for neutralization. The aqueous layer was extracted with dichloromethane. The crude product was purified by silica gel column chromatography to give the desired N-(2-chloro-5-pyridylmethyl)-N-methyl-N'-(1-benzylthio-2-nitrovinyl)ethylenediamine (0.3 g) having a melting point of 119° to 123° C.

Compounds of formula (I) in accordance with this invention which were produced by the same methods as in Examples 1 to 5 are shown in Table 1 below together with the compounds obtained in Examples 1 to 5.

TABLE 1

$$W^1-CH-N-A-N-C-X-R^4$$
$$\phantom{W^1-CH-}\underset{R^1}{|}\phantom{-N-}\underset{R^2}{|}\phantom{-A-}\underset{R^3}{|}\phantom{-N-}\underset{Y-Z}{\|}$$

| Comp. No. | W¹ | R¹ | R² | A | R³ | Y—Z | X | R⁴ | Physical constant |
|---|---|---|---|---|---|---|---|---|---|
| 1 | 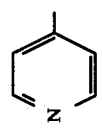 | H | —CH₃ | —CH₂CH₂— | H | =CH—NO₂ | S | —CH₃ | mp. 126~129° C. |
| 2 | 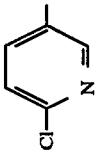 | H | H | —CH₂CH₂— | H | =CH—NO₂ | S | H | mp. 136~137° C. (decomp) |
| 3 | 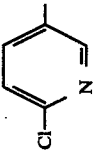 | H | H | —CH₂CH₂CH₂— | H | =CH—NO₂ | S | H | mp. 131~135° C. (decomp) |
| 4 | 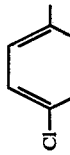 | H | —CH₃ | —CH₂CH₂— | H | =CH—NO₂ | S | —CH₃ | mp. 93~95° C. |
| 5 | 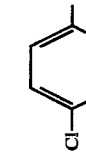 | H | —CH₃ | —CH₂CH₂CH₂— | H | =CH—NO₂ | S | —CH₃ | |
| 6 | 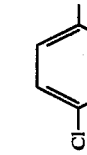 | H | —C₂H₅ | —CH₂CH₂— | H | =CH—NO₂ | S | —CH₃ | |
| 7 | 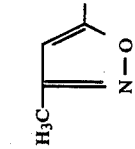 | H | —CH₃ | —CH₂CH₂— | H | =CH—NO₂ | S | —CH₃ | mp. 81~84° C. |

TABLE 1-continued $$W^1-\overset{R^1}{\underset{|}{CH}}-N-A-\overset{R^3}{\underset{|}{N}}-\underset{\underset{Y-Z}{\overset{\|}{C}}}{C}-X-R^4$$

| Comp. No. | W¹ | R¹ | R² | A | R³ | Y—Z | X | R⁴ | Physical constant |
|---|---|---|---|---|---|---|---|---|---|
| 8 | (2-chloro-thiazolyl) | H | —CH₃ | —CH₂CH₂CH₂— | H | =CH—NO₂ | S | —CH₃ | mp. 113~116° C. |
| 9 | (6-chloro-pyridyl) | H | —CH₃ | —CH₂CH₂— | H | =CH—NO₂ | S | —C₂H₅ | mp. 65~67° C. |
| 10 | (6-chloro-pyridyl) | H | —CH₃ | —CH₂CH₂— | H | =CH—NO₂ | S | —C₃H₇—n | $n_D^{20}$ 1.6055 |
| 11 | (6-chloro-pyridyl) | H | —CH₃ | —CH₂CH₂— | H | =CH—NO₂ | S | —C₃H₇—iso | $n_D^{20}$ 1.6080 |
| 12 | (6-chloro-pyridyl) | H | —CH₃ | —CH₂CH₂— | H | =CH—NO₂ | S | —CH₂—C₆H₅ | mp. 119~123° C. |
| 13 | (6-chloro-pyridyl) | H | —C₂H₅ | —CH₂CH₂— | H | =CH—NO₂ | S | —CH₂—(6-chloro-pyridyl) | |
| 14 | (6-chloro-pyridyl) | H | —CH₃ | —CH₂CH₂— | —CH₃ | =CH—NO₂ | S | —CH₃ | $n_D^{20}$ 1.6273 |

TABLE 1-continued $$W^1-\overset{R^1}{\underset{|}{C}H}-\overset{R^2}{\underset{|}{N}}-A-\overset{R^3}{\underset{|}{N}}-\underset{\underset{Y-Z}{\|}}{C}-X-R^4$$

| Comp. No. | W¹ | R¹ | R² | A | R³ | Y—Z | X | R⁴ | Physical constant |
|---|---|---|---|---|---|---|---|---|---|
| 15 | 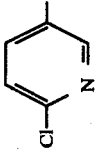 | H | —CH₃ | —CH₂CH₂— | H | =CH—NO₂ | NH | H | mp. 120~123° C. |
| 16 | 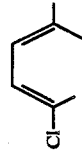 | H | —CH₃ | —CH₂CH₂— | H | =CH—NO₂ | NH | —CH₃ | mp. 126~128° C. |
| 17 | 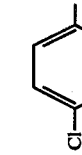 | H | —CH₃ | —CH₂CH₂— | H | =CH—NO₂ | N—CH₃ | —CH₃ | mp. 79~86° C. |
| 18 | 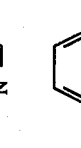 | H | —CH₃ | —CH₂CH₂— | H | =CH—NO₂ | NH | —N(CH₃)₂ | |
| 19 | 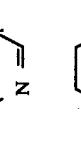 | H | —CH₃ | —CH₂CH₂— | H | =CH—NO₂ | NH | 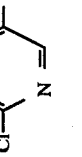 | mp. 179~182° C. |
| 20 | | H | —CH₃ | —CH₂CH₂— | H | =CH—NO₂ | — | —CH₃ | mp. 78~80° C. |
| 21 | | H | —CH₃ | —CH₂CH₂— | H | =CH—NO₂ | — | 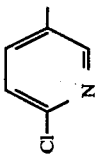 | $n_D^{20}$ 1.5685 |

TABLE 1-continued $$W^1-CH-N-A-N-C-X-R^4$$
$$\phantom{W^1-CH-}R^1\phantom{-N-}R^2\phantom{-A-N-}R^3\phantom{-C-X-R^4}$$
$$\phantom{W^1-CH-N-A-N-}\underset{Y-Z}{\|}$$

| Comp. No. | W¹ | R¹ | R² | A | R³ | Y—Z | X | R⁴ | Physical constant |
|---|---|---|---|---|---|---|---|---|---|
| 22 | 5-chloro-2-pyridyl | H | —C₂H₅ | —CH₂CH₂— | H | =N—CN | S | —CH₃ | $n_D^{20}$ 1.5938 |
| 23 | | 3-pyridyl-CH₂—N(CH₃)—CH₂CH₂—NH—C(=CHNO₂)—NH—CH₂CH₂—N(CH₃)—CH₂-3-pyridyl | | | | | | | |
| 24 | | 6-chloro-3-pyridyl-CH₂—N(CH₃)—CH₂CH₂—NH—C(=CHNO₂)—NH—CH₂CH₂—N(CH₃)—CH₂-6-chloro-3-pyridyl | | | | | | | mp. 124~127° C. |
| 25 | | 6-chloro-3-pyridyl-CH₂—N(CH₃)—CH₂CH₂—N(CH₃)—C(=CHNO₂)—N(CH₃)—CH₂CH₂—N(CH₃)—CH₂-6-chloro-3-pyridyl | | | | | | | $n_D^{20}$ 1.5733 |
| 26 | 6-chloro-3-pyridyl | H | —CH₃ | —CH₂CH₂— | H | =CH—NO₂ | NH | —OCH₃ | $n_D^{20}$ 1.5466 |
| 27 | 6-fluoro-3-pyridyl | H | —CH₃ | —CH₂CH₂— | H | =CH—NO₂ | S | —CH₃ | |
| 28 | 6-methyl-3-pyridyl | H | —CH₃ | —CH₂CH₂— | H | =CH—NO₂ | S | —CH₂CH₂OC₂H₅ | |

TABLE 1-continued $$W^1-CH-N-A-N-C-X-R^4$$
$$\phantom{W^1-CH-N-A-N-}\overset{|}{R^1}\phantom{-}\overset{|}{R^2}\phantom{-}\overset{|}{R^3}\phantom{-}\overset{\|}{Y-Z}$$

| Comp. No. | W¹ | R¹ | R² | A | R³ | Y—Z | X | R⁴ | Physical constant |
|---|---|---|---|---|---|---|---|---|---|
| 29 | 5-(F₃C)-pyridin-2-yl | H | —CH₃ | —CH₂CH₂— | H | =CH—NO₂ | S | —CH₂CH₂SC₂H₅ | |
| 30 | 5-(CH₃O)-pyridin-2-yl | H | —CH₃ | —CH₂CH₂— | H | =CH—NO₂ | S | —CH₃ | |
| 31 | 5-(CH₃S)-pyridin-2-yl | H | —CH₃ | —CH₂CH₂— | H | =CH—NO₂ | S | —CH₃ | |
| 32 | 1-CH₃-pyrazol-3-yl | H | —CH₃ | —CH₂CH₂CH₂— | H | =CH—NO₂ | S | —CH₃ | |
| 33 | 1-(CH₃)₂CH-pyrazol-3-yl | —CH₃ | —CH₃ | —CH₂CH₂— | H | =CH—NO₂ | S | —CH₃ | |
| 34 | isoxazol-3-yl | H | —CH₃ | —CH₂CH₂— | H | =CH—NO₂ | S | —CH₃ | |
| 35 | 1,2,5-thiadiazol-3-yl | H | —C₂H₅ | —CH₂CH₂— | H | =CH—NO₂ | S | —CH₃ | |

TABLE 1-continued
$$W^1-\overset{R^1}{\underset{|}{CH}}-\overset{R^2}{\underset{|}{N}}-A-\overset{R^3}{\underset{|}{N}}-\overset{||}{\underset{Y-Z}{C}}-X-R^4$$
| Comp. No. | W¹ | R¹ | R² | A | R³ | Y—Z | X | R⁴ | Physical constant |
|---|---|---|---|---|---|---|---|---|---|
| 36 | 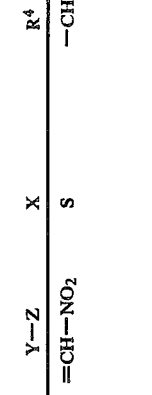 | H | —CH₃ | —CH₂CH₂— | H | =CH—NO₂ | S | —CH₃ | |
| 37 | 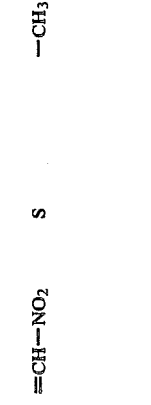 | H | —CH₃ | —CH₂CH₂— | H | =CH—NO₂ | S | —CH₃ | |
| 38 |  | H | —CH₃ | —CH₂CH₂— | H | =CH—NO₂ | S | —CH₃ | |
| 39 | 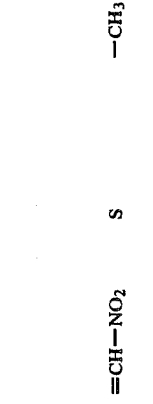 | H | —CH₃ | —CH₂CH₂— | H | =CH—NO₂ | S | —CH₃ | |
| 40 | 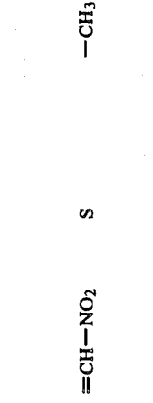 | H | —CH₃ | —CH₂CH₂— | —CH₃ | =CH—NO₂ | S | —CH₃ | |
| 41 | 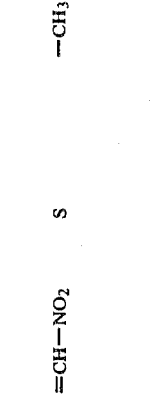 | H | —CH₃ | —CH₂CH₂— | H | =CH—NO₂ | S | —CH₃ | |
| 42 | 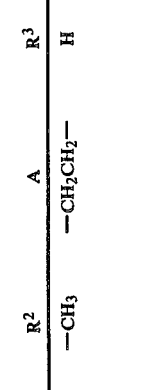 | H | —CH₃ | —CH₂CH₂— | H | =CH—NO₂ | S | —CH₃ | |

TABLE 1-continued
$$W^1-CH-N-A-N-C-X-R^4$$
$$\phantom{W^1-CH-N-A-N-}\overset{\|}{Y-Z}$$
with R¹, R², R³ substituents
| Comp. No. | W¹ | R¹ | R² | A | R³ | Y=Z | X | R⁴ | Physical constant |
|---|---|---|---|---|---|---|---|---|---|
| 43 | 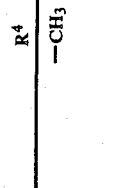 | H | —CH₃ | —CH₂C—CH₂—<br>CH₃ CH₃ | H | =CH—NO₂ | S | —CH₃ | |
| 44 |  | —CH₃ | —CH₃ | —CH₂CH₂— | H | =CH—NO₂ | S | —CH₃ | |
| 45 | 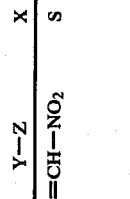 | H | —CH₃ | —CH₂CH₂— | —CH₃ | =CH—NO₂ | NH | H | |
| 46 | 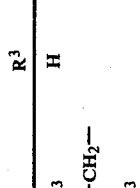 | H | —CH₃ | —CH₂CH₂— | H | =CH—NO₂ | NH | —OCH₃ | |
| 47 | 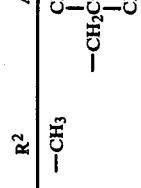 | H | —CH₃ | —CH₂CH₂— | H | =CH—NO₂ | NH | —C₃H₇—iso | |
| 48 | 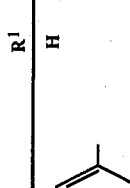 | H | —CH₃ | —CH₂CH₂CH₂— | H | =CH—NO₂ | NH | —N(CH₃)₂ | |
| 49 | 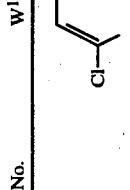 | H | —CH₃ | —CH₂CH₂— | H | =N—NO₂ | NH | H | |

TABLE 1-continued $$W^1-\overset{R^1}{\underset{|}{CH}}-N-A-\overset{R^3}{\underset{|}{N}}-\overset{}{\underset{\parallel}{C}}-X-R^4$$
$$\phantom{W^1-CH-N-A-N-C}Y-Z$$

| Comp. No. | W¹ | R¹ | R² | A | R³ | Y—Z | X | R⁴ | Physical constant |
|---|---|---|---|---|---|---|---|---|---|
| 50 | H₃C-pyridine | H | —CH₃ | —CH₂CH₂— | H | =N—NO₂ | NH | H | |
| 51 | H₃C-N-pyrazole | H | —CH₃ | —CH₂CH₂— | H | =N—NO₂ | NH | H | |
| 52 | H₃C-isoxazole N—O | H | —CH₃ | —CH₂CH₂— | H | =N—NO₂ | NH | H | |
| 53 | H₃C-pyrimidine | H | —CH₃ | —CH₂CH₂— | H | =N—NO₂ | NH | H | |
| 54 | Cl-pyridine | H | —CH₂ | —CH₂CH₂— | H | CN / =C—CN | S | —CH₃ | |
| 55 | Cl-pyridine | H | —CH₃ | —CH₂CH₂— | H | COOC₂H₅ / =C—CN | S | —CH₃ | |
| 56 | thiazole | H | —CH₃ | —CH₂CH₂— | H | CN / =C—CN | S | —C₂H₅ | |

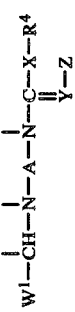

TABLE 1-continued

W¹—CH—N—A—N—C—X—R⁴
     |   |   |   ||
     R¹ R² R³  Y—Z

| Comp. No. | W¹ | R¹ | R² | A | R³ | Y—Z | X | R⁴ | Physical constant |
|---|---|---|---|---|---|---|---|---|---|
| 57 | 5-bromo-2-pyridyl | H | —CH₃ | —CH₂CH₂— | H | =N—CN | S | —CH₃ | |
| 58 | 2-chlorothiazol-5-yl | H | —CH₃ | —CH₂CH₂— | H | =N—CN | S | —CH₃ | |
| 59 | 3-methylisoxazol-5-yl | H | —CH₃ | —CH₂CH₂— | H | =N—CN | S | —CH₃ | |
| 60 | 5-methylpyrazin-2-yl | H | —CH₃ | —CH₂CH₂— | H | =N—CN | S | —CH₃ | |

EXAMPLE 6

Synthesis of a starting material:

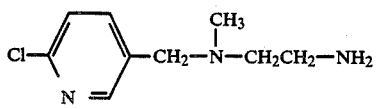

A solution of 2-chloro-5-chloromethylpyridine (3.2 g) in 30 ml of acetonitrile was added dropwise to a solution of N-methylethylenediamine (7.4 g) in acetonitrile (50 ml) with good stirring at 5° to 10° C. After the addition, the mixture was stirred at room temperature for 2 hours. From the mixture, first the acetonitrile and then the excess of N-methylethylenediamine were evaporated under reduced pressure (the temperature of the reaction mixture lower than 50° C.). Dichloromethane was added to the residue, and the mixture was washed twice with a small amount of water, and then dried. Evaporation of dichloromethane gave the desired N-2-chloro-5-pyridylmethyl-N-methylethylenediamine (2.7 g) as a colorless oil having an $n_D^{22}$ of 1.5584.

Biological tests

EXAMPLE 7

Test on *Nephotettix cincticeps* having resistance to organophosphorus agents:

Preparation of a test chemical

Solvent: 3 parts by weight of xylene

Emulsifier: 1 part by weight of polyoxyethylene alkyl phenyl ether

To form a suitable preparation, 1 part by weight of the active compound was mixed with the aforesaid amount of the solvent contaning the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the kill ratio was calculated.

In this test, for example, the Compounds No. 1, 2, 3, 4, 5, 6, 7, 10, 11, 12, 13, 15, 16, 18, 19, 20, 22, 24 and 25 exhibited a kill ratio of 100% at a concentration of 200 ppm of the active ingredient.

EXAMPLE 8

Test on Planthoppers:

Testing method

A water dilution in a predetermined concentration of the active compound prepared as in Example 7 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to organophosphorus chemicals were released into the net. The pots were left to stand in a constant temperature chamber and the number of dead insects was examined two days later. The kill ratio was then calculated.

In the same way as above, the kill ratio was calculated on *Sogatella furcifera* Horvath and organophosphorus-resistant *Laodelphax striatellus* Fallen.

In this test, for example, the compounds No. 1, 2, 3, 4, 6, 7, 9, 10, 11, 12, 13, 17, 18, 19 and 26 exhibited a kill ratio of 100% at a concentration of 200 ppm of the active ingredient against *N. lugens, S. furcifera* and *L. striatellus*.

EXAMPLE 9

Test on *Myzus perisicas* (green peach aphids) having resistance to organophosphorus chemicals and carbamate chemicals:

Testing method

Green peach aphids which had been bred and had resistance to organophosphorus chemicals and carbamate chemicals were inoculated on eggplant seedlings (black elongate eggplants), about 20 cm tall, grown in unglazed pots having a diameter of 15 cm (about 200 aphids per seedling). One day after the inoculation, a water dilution of each active compound at a predetermined concentration prepared as in Example 7 was sprayed in a sufficient amount onto the plants using a spray gun. After the spraying, the pots were left to stand in a greenhouse at 28° C. Twenty-four hours after the spraying, the kill ratio was calculated. For each compound, the test was carried out through two replicates.

In this test for example the compounds No. 2, 4, 6, 7, 9, 10 and 12 exhibited a kill ratio of 100% at a concentration of 200 ppm of the active ingredient.

We claim:

1. An alkylenediamino of the formula

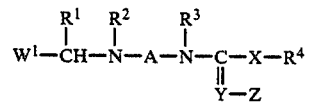

wherein $R^1$, $R^2$ and $R^3$ represents hydrogen or $C_{1-4}$ alkyl, $R^4$ represents hydrogen, $C_{1-4}$ alkyl, $C_{6-10}$ aryl, benzyl, phenethyl, $C_{1-4}$ alkoxy, dialkylamino having 2 to 6 carbon atoms in total, alkoxyalkyl having 2 to 6 carbon atoms in total, alkylthioalkyl having 2 to 4 carbon atoms in total or a group of the formula —$CH_2$—$W^2$ in which $W^2$ has the same meaning as $W^1$ X represents S or a single bond, Y represents N or

in which $R^6$ represents hydrogen, $C_{1-4}$ alkyl, $C_{6-10}$ aryl, $C_{1-4}$ alkylcarbonyl, alkoxycarbonyl having $C_{1-4}$ alkoxy or cyano, Z represents cyano or nitro, $W^1$ represents pyridyl, the group $W^1$ being unsubstituted or substituted by at least one substituent selected from halogen, $C_{1-4}$ alkyl, $C_{1-4}$ alkoxy, $C_{1-4}$ alkylthio, $C_{1-4}$ haloalkyl and $C_{1-4}$ haloalkoxy, and A represents ethylene which may be unsubstituted or substituted by methyl or trimethylene which may optionally be substituted by methyl.

2. An alkylenediamine according to claim 1, wherein R$^1$, R$^2$, and R$^3$ represent hydrogen, methyl or ethyl, R$^4$ represents hydrogen, methyl, ethyl, phenyl, benzyl, methoxy, dimethylamino, 1-ethoxyethyl, 1-ethyl-thioethyl or 2-chloro-5-pyridylmethyl, X represents S, Y represents N or

in which R$^6$ represents hydrogen, methyl, phenyl, acetyl, ethoxycarbonyl or cyano, Z represents cyano or nitro, W$^1$ represents pyridyl, the group W$^1$ being unsubstituted or substituted by at least one substituent selected from fluoro, chloro, bromo, methyl, methylthio, trifluoromethyl and trifluoromethoxy, and A represents ethylene or trimethylene.

3. An alkylenediamine according to claim 1 selected from one of the following compounds:

(a) N-(2-chloro-5-pyridylmethyl)-N-methyl-N'-(1-methylthio-2-nitrovinyl)ethylenediamine which is represented by the formula

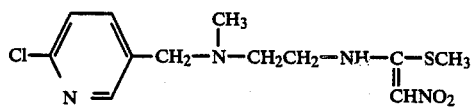

(b) N-(2-chloro-5-pyridylmethyl)-N-ethyl-N'-(1-methylthio-2-nitrovinyl)ethylenediamine which is represented by the formula

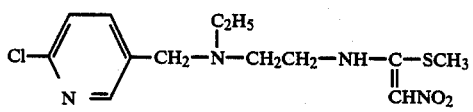

(c) N-(2-chloro-5-pyridylmethyl)-N'-(1-mercapto-2-nitrovinyl)ethylenediamine which is represented by the formula

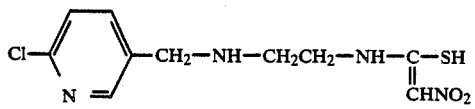

(d) N-(2-chloro-5-pyridylmethyl)-N'-(1-mercapto-2-nitrovinyl)trimethylenediamine which is represented by the formula

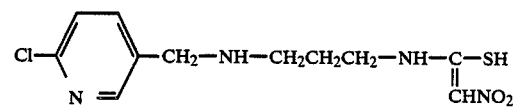

(e) N-(2-chloro-5-pyridylmethyl)-N-methyl-N'-(1-ethylthio-2-nitrovinyl)ethylenediamine which is represented by the formula

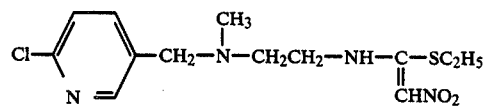

(f) N-(2-chloro-5-pyridylmethyl)-N-methyl-N'-(1-propylthio-2-nitrovinyl)ethylenediamine which is represented by the formula

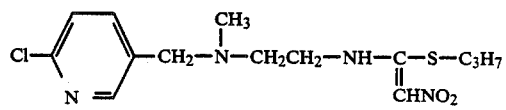

4. An insecticidal composition, comprising an insecticidally effective amount of at least one alkylenediamine according to claim 1 and a suitable extender or surface active agent.

5. A method for combating harmful insects, comprising applying to said insects or to the habitat thereof an effective amount of an alkylenediamine according to claim 1.

* * * * *